United States Patent [19] [11] 3,994,913
Beck et al. [45] Nov. 30, 1976

[54] 2,5-DICHLORO-THIAZOLO[4,5-d] THIAZOLE AND PROCESS FOR MAKING SAME
[75] Inventors: Gunther Beck; Helmut Heitzer, both of Leverkusen; Hans Holtschmidt, Bergisch-Gladbach, all of Germany
[73] Assignee: Bayer Aktiengesellschaft, Leverkusen, Germany
[22] Filed: Oct. 28, 1975
[21] Appl. No.: 626,410

[30] Foreign Application Priority Data
Oct. 30, 1974 Germany............................ 2451635

[52] U.S. Cl. .................... 260/306.8 F; 260/566 D; 424/270
[51] Int. Cl.² ........................................ C07D 513/04
[58] Field of Search............................. 260/306.8 F

[56] References Cited
UNITED STATES PATENTS
3,829,435  8/1974  Beck et al. ................... 260/306.8 F Primary Examiner—R. Gallagher
Attorney, Agent, or Firm—Burgess, Dinklage & Sprung

[57] ABSTRACT 2,5-Dichloro-thiazolo[4,5-d]thiazole, which is useful as a fungicide, is prepared by reacting compounds having the formula

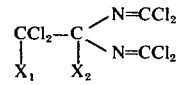

wherein
$X_1$ is Cl, and
$X_2$ is H or Cl or
$X_1$ and $X_2$ together form a C—C bond
in the temperature range of 150° to 300° C, with at least the stoichiometrically required amount of sulphur.

3 Claims, No Drawings

2,5-DICHLORO-THIAZOLO[4,5-d]THIAZOLE AND PROCESS FOR MAKING SAME

This invention relates to 2,5-dichlorothiazolo[4,5-d]-thiazole and a process for its preparation.

SUMMARY 2,5-dichloro-thiazolo[4,5-d]-thiazole of the formula I

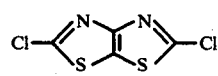

may be obtained by reacting a compound of the general formula II

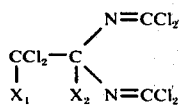

wherein
$X_1$ represents Cl and
$X_2$ represents H or Cl or
$X_1$ and $X_2$ together denote a C—C bond with sulphur at a temperature of from 150° to 300° C, preferably of from 170° to 270° C.

DESCRIPTION

As compounds of the general formual II there may be mentioned: trichloroethylidene-bis-(isocyanide-dichloride), tetrachloroethylidene-bis-(isocyanide-dichloride) and dichlorovinylidene-bis-(isocyanide-dichloride).

The process according to the invention can be represented, for example, by the following equations:

The abovementioned starting compounds of the general formula (II) can, for example, be prepared in good yields by the following method, starting from the known trichloroethylidene-bis-formamide, which is obtainable by reaction of 1 mol of chloral with 2 mols of formamide (compare Annales de Chimie et de Physique, 6th series, volume 27, page 326; compare Beilsteins Handbuch der Organischen Chemie (Beilstein's Handbook of Organic Chemistry), 4th edition, volume 2, page 27):

Trichloroethylidene-bis-(isocyanide-dichloride) is obtainable from trichloroethylidene-bis-formamide by reaction with an acid chloride, for example phosphorus pentachloride, in a diluent such as, for example, carbon tetrachloride, whilst at the same time passing in an excess of chlorine gas, at 0° – 150° C (compare Example 1).

Tetrachloroethylidene-bis-(isocyanide-dichloride) is obtainable from the abovementioned trichloroethylidene-bis-(isocyanide-dichloride) by reaction with chlorine at 150° – 200° C (compare Example 2).

Dichlorovinylidene-bis-(isocyanide-dichloride) is obtainable from tetrachloroethylidene-bis-(isocyanide-dichloride) by dechlorination at 150° –250° C, for example with elementary phosphorus (compare Example 3).

The process according to the invention is in general carried out in bulk, without solvents. It is, however, also possible to work in the presence of organic solvents which boil in the temperature range used and are inert towards the reactants. For example, it is possible to work in the presence of naphthalene and/or methyl-naphthalenes and/or acenaphthylene and/or diphenyl. Of course, the process can also be carried out continuously.

The process according to the invention can be carried out, for example, by mixing compounds of the general formula (II), or mixtures of the compounds in question, with at least the stoichiometrically required amount of sulphur and heating the mixture to temperatures of, preferably, 170° to 270° C. Suitably, the mixture is heated, whilst distilling off the sulphur chloride produced, until no further sulphur chloride distils over.

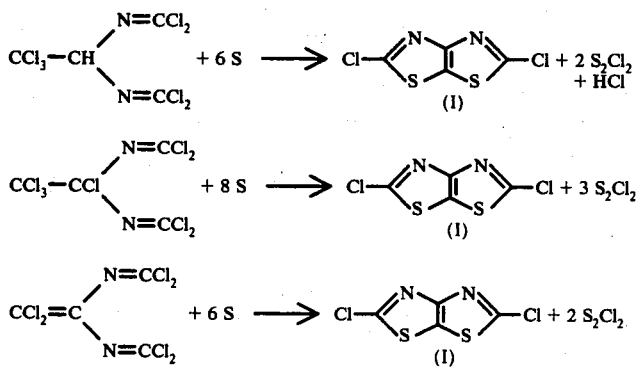

In accordance with these equations, in general 6 or 8 mols of sulphur, respectively, are employed at the stoichiometrically required amount, per mol of the starting compound, for the process according to the invention. It has proved suitable to employ the sulphur in at least the stoichiometrically required amount or in an excess of about 5 to 10%.

The end of the reaction can be established in a simple manner by IR spectrometry from the disappearance of the bands in the region between 1,600 and 1,650 cm$^{-1}$ which are characteristic of the isocyanide-dichloride compounds.

The reaction mixtures obtained in accordance with the process of the invention can be worked up by, for example, fractional distillation and/or crystallisation. Any admixed excess sulphur can easily be removed by dissolving it out with carbon disulphide. It is, however, also possible to pass chlorine into a suspension of (I) and sulphur in, for example, carbon tetrachloride under reflux until all the sulphur has been converted to sulphur chloride, and then to isolate the desired product in the pure form by filtering it off.

2,5-Dichloro-thiazolo[4,5-d]thiazole, to which the invention relates, is new and is useful as a fungicide. (See Example 4). In addition, because of its bifunctionality, the compound of the invention is distinguished by being a valuable intermediate product and is suitable for the synthesis of plastics having interesting properties, for example plastics based on condensation products with diols or polyols or diamines or polyamines. The following examples illustrate the invention.

EXAMPLE 1

A mixture of 100 g (0.308 mol) of trichloroethylidene-bis-(isocyanide-dichloride) and 65 g (2.03 mols) of sulphur is fused in a stirred apparatus having an attached distillation bridge and is then brought to the reaction temperature of about 250° C whilst stirring, in the course of which the disulphur dichloride formed distils off partially. The reaction mixture is then kept at 240° to 250° C for a further 8 hours, after which is allowed to cool, and the residual disulphur dichloride is distilled off in a waterpump vacuum. The crude product is then distilled from the reaction mixture at about 0.1 mm Hg until the sump temperature is 250° C. About 67 g of crude product are obtained and are in the first place recrystallised from hexane. The crystalline product thus obtained is then washed with carbon disulphide, as a result of which sulphur which has also crystallised out is dissolved away. 36 g (55.4% of theory) of pure 2,5-dichloro-thiazolo[4,5-d]thiazole of melting point 180° C are obtained. The empirical formula $C_4Cl_2N_2S_2$ is confirmed by the mass spectrum. The compound shows a very characteristic IR spectrum with sharp bands at (in cm$^{-1}$): 1,468 st, 1,432 st, 1,378 m, 1,089 st, 1,030 st, 990 m, 701 w, 682 w, 641 w, 415 w (st = strong, m = medium, w = weak).

The UV spectrum shows the following absorption bands (in cyclohexane):

$\nu_{max_1} = 36,900$ cm$^{-1}$, $\nu_{max_2} = 44,350$ cm$^{-1}$,
$\epsilon_{max_1} = 8,050$;
$\epsilon_{max_2} = 18,900$.

The trichloroethylidene-bis-(isocyanide-dichloride) used as the starting material is obtained as follows:

439 g (2 mols) of trichloroethylidene-bis-formamide are added in small portions, over the course of about 2 –3 hours, to a suspension, boiling under reflux (about 81° C) and saturated with chlorine gas, of 1,000 g (4.8 mols) of phosphorus pentachloride in 2,000 ml of carbon tetrachloride, whilst excluding moisture and constantly continuing to pass in excess chlorine. In the course thereof the boiling point rises to 84° C. Whilst constantly continuing to pass a stream of chlorine into the reaction mixture, the carbon tetrachloride and the phosphorus oxychloride formed are distilled off over the course of 1.5 to 2 hours, during which the temperature is raised to about 150° C. This temperature is maintained for a further hour, sulphur dioxide is then passed in at about 100° to 120° C to decompose the excess phosphorus pentachloride and at the same time the SOCl$_2$ and POCl$_3$ formed are distilled off. 660 g of a crude product are obtained from the reaction mixture by fractional distillation up to material passing over at 137° C/13 mm Hg; this crude product contains, according to a gas chromatogram, 589 g (corresponding to 90.6% of theory) of trichloroethylidene-bis-(isocyanide-dichloride). The latter is isolated by fractional vacuum distillation of the crude product (boiling point: 136°–137° C/13 mm Hg). Recrystallisation from petroleum ether gives colourless crystals of melting point 90° C. The empirical formula of the compound ($C_4HCl_7N_2$) is confirmed by the mass spectrum.

The compound shows a characteristic IR spectrum with the following bands (in cm$^{-1}$): 2,910 w, 1,655 st, 1,625 st, 1,330 w, 1,310 m, 1,065 w, 1,050 m, 895 st, 810 st, 650 m, 595 m, 550 w, 535 w, 510 w (st = strong, m = medium, w = weak).

The nuclear resonance spectrum ($^1$H—NMR) in CCl$_4$ shows a signal at $\delta = 5.5$ ppm relative to TMS.

EXAMPLE 2

A mixture of 1,080 g (3 mols) of tetrachloroethylidene-bis-(isocyanide-dichloride) and 806 g (25.2 mols) of sulphur is kept for 4 hours at 205° to 210° C in a stirred apparatus having an attached distillation bridge, during which time the disulphur dichloride formed distils off partially. Thereafter, as described in Example 1, first the residual disulphur dichloride and then the crude product are distilled off in vacuo. About 1 liter of carbon tetrachloride is added to the crude product (590 g) and chlorine is passed in under reflux at about 80° C until all excess sulphur has been converted to sulphur chloride (about 4 hours). The suspension is cooled to about 5° C and is filtered, and the crystals thus obtained are washed with cold CCl$_4$. The carbon tetrachloride used to wash the crystals is concentrated to dryness in a rotary evaporator in vacuo, and the crystals thereby obtained are digested with a little CCl$_4$, filtered off, also washed with carbon tetrachloride and dried. A total of 438 g of 2,5-dichlorothiazolo[4,5-d]thiazole of melting point 180° C is obtained. The total yield is accordingly about 69% of theory.

The tetrachloroethylidene-bis-(isocyanide-dichloride) used as the starting material is obtained as follows:

A constant excess (detectable from the green colour of the gas which issues) of chlorine is passed as a stream into a melt of 1,463 g (4.5 mols) of trichloroethylidene-bis-(isocyanide-dichloride) at 180° C in a quartz flask, whilst stirring and under exposure to a 400 watt daylight lamp (Osram). When no further starting material is detectable by analysis by gas chromatography, the excess chlorine is displaced by passing in a dry stream of nitrogen and the reaction mixture is subjected to fractional distillation. At boiling point 148° to 149° C/12 mm Hg, 1,565 g of tetrachloroethylidene-bis-(isocyanide-dichloride) (corresponding to 96.6% of theory) are obtained as a colourless liquid.

The empirical formula of the compound ($C_4Cl_8N_2$) is confirmed by the mass spectrum.

EXAMPLE 3

A mixture of 72.3 g (0.25 mol) of dichlorovinylidene-bis-(isocyanide-dichloride) and 50.5 g (1.58 mols) of sulphur is heated in a stirred apparatus having an attached distillation bridge. The formation of sulphur chloride is noted at about 190° C. The mixture is kept at between 205° and 210° C for 3 hours, during which the disulphur dichloride formed distils off partially. Thereafter, as described in Example 1, the residual disulphur dichloride, followed by the crude product, are distilled off in vacuo. Chlorine is passed into the suspension of the crude product (55 g) in 200 ml of carbon tetrachloride under reflux to about 1 hour at 80° C. The further working up is carried out as in Example 2, and gave 38 g (corresponding to 72.1% of theory) of pure 2,5-dichloro-thiazolo[4,5-d]thiazole of melting point 180° C.

The dichlorovinylidene-bis-(isocyanide-dichloride) used as starting material is obtained as follows:

A suspension of 36 g (1.16 mols) of red, finely powdered phosphorus in 320 g (0.89 mol) of tetrachloroethylidene-bis-(isocyanide-dichloride) is heated under an approx. 60 cm long Vigreux column fitted with a dephlegmator. The reaction starts at about 180° C with foaming and a slight rise in temperature to about 190° C. The reaction is allowed to continue for about ½ hour longer and phosphorus trichloride is then distilled off (74° –75° C) slowly over the course of 4 hours, during which the temperature of the reaction mixture rises to about 215° C. At that stage, no further starting material is detectable by analysis by gas chromatography. Fractional distillation of the reaction mixture gives 221 g (corresponding to 86% of theory) of dichlorovinylidene-bis-(isocyanide-dichloride) as a colourless liquid. Boiling point 121° – 122° C/15 mm Hg. the empirical formula of the compound ($C_4Cl_6N_2$) is confirmed by the mass spectrum.

EXAMPLE 4

Botrytis test:

2,5-Dichloro-thiazolo[4,5-d]thiazole is dissolved in 4.7 parts by weight of acetone and 0.3 part by weight of alkylaryl polyglycol ether and the concentrate is diluted with 95 parts by weight of water so that the resulting concentration of active compound in the spray liquor is 0.0025%.

Young Vicia faba bean plants of the Zwijndrechter variety, having 3 – 4 pairs of leaves, are sprayed with the spray liquor until dripping wet. After 24 hours, the pairs of leaves are pulled off and the individual leaves are placed in Petri dishes, the lid and bottom of which are lined with moist discs of filter paper. Discs of filter paper of 1 cm diameter are dipped into an aqueous suspension of Botrytis cinerea, and placed on the treated leaves lying in Petri dishes. After 48 hours' incubation at +20° C, the necroses visible under the discs are assessed.

The result found is that at an active compound concentration of 0.0025% the infection is 45% of the infection of the untreated leaves of the control experiment.

What is claimed is:

1. 2,5-Dichloro-thiazolo[4,5-d]thiazole.
2. Process for preparing 2,5-dichloro-thiazolo[4,5-d]thiazole which comprises reacting compounds having the formula

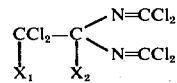

wherein
$X_1$ is Cl, and
$X_2$ is H or Cl or
$X_1$ and $X_2$ together form a C—C bond in the temperature range of 150° to 300° C, with at least the stoichiometrically required amount of sulphur.
3. Process of claim 2 carried out at 170° to 270° C.

* * * * *